(12) United States Patent
Kato et al.

(10) Patent No.: US 7,805,034 B2
(45) Date of Patent: Sep. 28, 2010

(54) OCT PROBE FOR ELIMINATING GHOST IMAGES

(75) Inventors: Kiichi Kato, Ashigarakami-gun (JP); Yoshinori Morimoto, Ashigarakami-gun (JP); Hiroshi Yamazaki, Kuroishi (JP); Masahiro Saito, Kuroishi (JP)

(73) Assignees: FUJIFILM Corporation, Tokyo (JP); Namiki Seimitsu Houseki Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/361,105

(22) Filed: Jan. 28, 2009

(65) Prior Publication Data
US 2009/0190883 A1    Jul. 30, 2009

(30) Foreign Application Priority Data
Jan. 29, 2008    (JP)    ............... 2008-017645

(51) Int. Cl.
*G02B 6/00* (2006.01)
*G02B 6/26* (2006.01)
(52) U.S. Cl. ......................... 385/31; 385/147
(58) Field of Classification Search ............ 385/31, 385/32, 33, 34, 35, 115–119
See application file for complete search history.

(56) References Cited

U.S. PATENT DOCUMENTS

| | | | |
|---|---|---|---|
| 5,321,501 A * | 6/1994 | Swanson et al. | 356/479 |
| 5,774,610 A * | 6/1998 | O'Rourke et al. | 385/52 |
| 6,445,939 B1 * | 9/2002 | Swanson et al. | 600/342 |
| 7,627,208 B2 * | 12/2009 | Kuroiwa | 385/31 |

FOREIGN PATENT DOCUMENTS

| | | |
|---|---|---|
| JP | 2004-223269 A | 8/2004 |
| JP | 2005-533610 A | 11/2005 |

* cited by examiner

*Primary Examiner*—Akm E Ullah
(74) *Attorney, Agent, or Firm*—Sughrue Mion, PLLC

(57) ABSTRACT

An OCT probe has a sheath to be inserted into a subject; and an optical system within the sheath, for changing the direction of light which propagates from a light source through an optical fiber to irradiate the light onto the subject through a transparent portion of the sheath, and for reflecting the light beam, which is reflected by the subject, to guide the light into the optical fiber. A light output surface, for causing the light to be output from the reflecting surface in a direction obliquely inclined with respect to the inner surface of the sheath, and a reflected light sheath entrance preventing portion, for preventing light reflected by the inner surface of the sheath from entering the optical fiber, are provided in the optical system. The reflected light sheath entrance preventing portion may be formed by providing a cut planar surface portion on the lens.

20 Claims, 6 Drawing Sheets

OCT PROBE FOR ELIMINATING GHOST IMAGES

BACKGROUND OF THE INVENTION

1. Field of the Invention

The present invention is related to an apparatus for observing tomographic structures using light. Particularly, the present invention is related to a probe for observing tomographic structures within living organisms.

2. Description of the Related Art

The utilization of images during medical examinations is becoming widespread. Consequently, the importance of non invasive, non contact observation techniques is increasing.

Conventionally, non invasive non contact observation and measurement of data within subjects such as living organisms had been performed by X rays. However, utilization of X rays has problems, such as the fact that subjects are irradiated with radiation, and that it is difficult to image the biological functions of the subjects. As a result, ultrasound endoscopic probes are in wide use for observation of tissue within body cavities. However, the spatial resolution of ultrasound endoscopic probes is not high, and it is not possible to obtain information of biological tissue except the shape thereof. Further, media such as water are necessary to utilize ultrasound endoscopic probes, and therefore, the processes involved in observation of subjects are complex.

Recently, various techniques related to OCT (Optical Coherence Tomography), which uses light to visualize information regarding structures within subjects' bodies have been proposed. PCT Japanese Publication No. 2005-533610 and Japanese Unexamined Patent Publication No. 2004-223269 disclose examples of OCT endoscopic probes. These OCT endoscopic probes are inserted into body cavities, then optical scanning is performed to image tomographic images of organ walls and the like.

Figure 6:
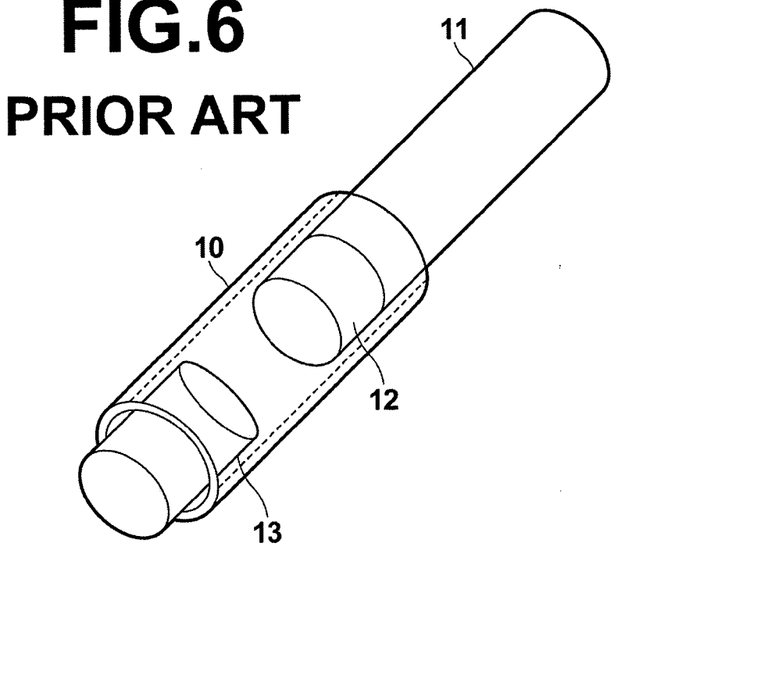
FIG. 6 is a perspective view that illustrates an example of a conventional OCT probe.

Specifically, PCT Japanese Publication No. 2005-533610 discloses an OCT endoscopic probe. As illustrated in FIG. 6 attached to the present application, the OCT endoscopic probe includes: a transparent cylindrical sheath 10; a single mode optical fiber 11 which is rotatably drivable; a lens 12 fixed to the tip of the optical fiber 11; and a beam director 13 (return mirror). The optical fiber 11, the lens 12, and the beam director 13 are housed within the sheath 10. Note that in this example, the beam director 13 is provided separate from the lens 12. Light that propagates through the optical fiber 11 and is emitted from the lens 12 in a converged state is reflected by the beam director 13, and output toward the outer peripheral directions of the sheath 10.

Figure 7:
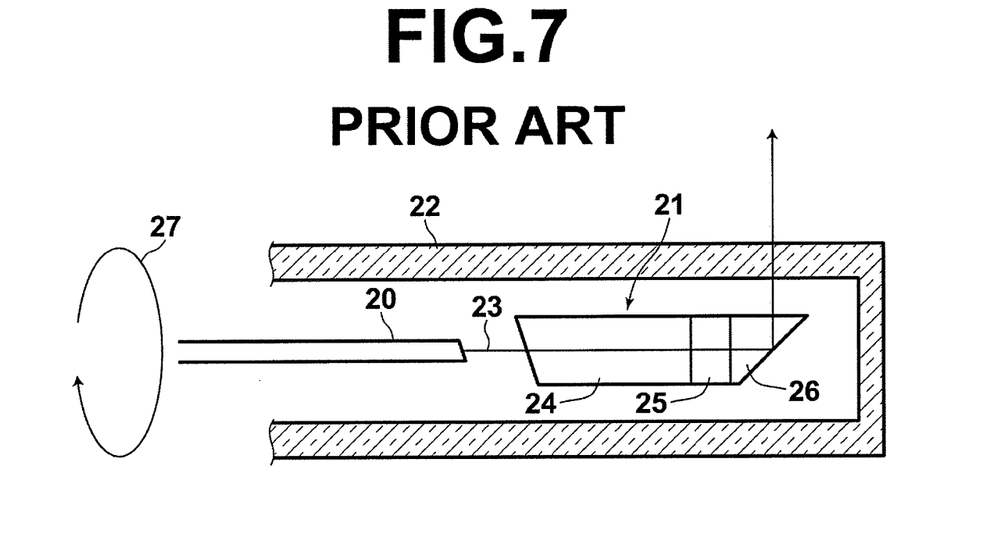
FIG. 7 is a partial sectional view that illustrates another example of a conventional OCT probe.

Japanese Unexamined Patent Publication No. 2004-223269 discloses another OCT endoscopic probe. This OCT endoscopic probe includes: a single mode optical fiber 20; a lens unit 21; and a transparent cylindrical sheath 22, as illustrated in FIG. 7. The tip of the optical fiber 20 and the lens unit 21 are housed within the sheath 22. In this OCT endoscopic probe, the lens unit 21 is constituted by: a GRIN (Gradient Index) lens 24, for focusing the light 23 output from the tip of the single mode optical fiber 20 onto living tissue; a Faraday rotator 25, for cancelling the effects of polarization due to bends in the single mode optical fiber 20; and a prism 26 for changing the direction that the light travels in. The single mode optical fiber 20 and the lens unit 21 rotate with the longitudinal direction (the longitudinal axis) of the sheath 22 as their rotational axis as indicated by arrow 27 of FIG. 7, to scan light in a cylindrical direction. Thereby, observation of measurement targets is enabled not only in the cross sectional direction but also as discoid shapes.

It is necessary for OCT endoscopic probes for medical and non medical use to have extended work distances (distances between light emitting ends and observation targets) and small spot sizes, in order to search through thin twisted paths such as arteries, veins, and pulmonary airways. It is expected that this demand will become even greater in the future. However, there is a problem that it is difficult for the OCT endoscopic probe disclosed in PCT Japanese Publication No. 2005-533610 to achieve a great work distance and small spot size.

Generally in OCT endoscopic probes, the correlations between reflective intensities along optical paths and optical path lengths are detected, which is the basic principle of OCT. Therefore, in cases that two surfaces that both reflect light strongly near each other, light is multiply reflected by these two reflective surfaces. This multiple reflection causes ghost images of the reflective surfaces at portions that do not actually exist, which significantly deteriorates observation properties. Particularly in cases that ghost images are displayed at the same locations as living tissue, it becomes impossible to distinguish between actual images of living tissue and the ghost images, which is a great problem.

Meanwhile, in the OCT endoscopic probe disclosed in Japanese Unexamined Patent Publication No. 2004-223269 (refer to FIG. 7), a light beam 23 which is output from the single mode fiber 20 is reflected a plurality of times at the boundary surfaces of optical elements such as the Faraday rotator 25, the GRIN lens 24, the prism 26, and the sheath 22, then returns to the single mode optical fiber 20. Therefore, images of living tissue and ghost images are overlapped, and there is a problem that the image quality of the images of living tissue is poor.

SUMMARY OF THE INVENTION

The present invention has been developed in view of the foregoing circumstances. It is an object of the present invention to prevent the generation of ghost images caused by multiple reflection, in OCT probes which are of configurations that irradiate light which has propagated through optical fibers and are irradiated onto subjects by passing through transparent portions of sheaths, and which are applied to endoscopes.

It is a further object of the present invention to extend the work distances and to decrease the diameters of spot sizes in OCT probes having the above configurations.

An OCT probe according to the present invention is an OCT probe which is equipped with an optical system that changes the direction of a light beam which has propagated from a light source through an optical fiber within a sheath with a reflecting surface, to irradiate the light beam onto the subject through a transparent portion of the sheath, and for reflecting the light beam, which has been reflected by the subject, at the reflecting surface to guide the light beam into the optical fiber; wherein the optical system is equipped with a light output surface for causing the light beam to be output from the reflecting surface in a direction obliquely inclined with respect to the inner surface of the sheath (if the fact that the light beam reflected by the subject also enters this surface is taken into consideration, this surface may also be referred to as a light output/input surface) and a reflected light sheath entrance preventing portion, which is a part of the optical system, for preventing light reflected by the inner surface of the sheath from entering the optical fiber.

Note that here, the phrase "preventing light reflected by the inner surface of the sheath from entering the optical fiber" means to prevent a large portion of the reflected light from entering the optical fiber.

Specifically, the reflected light sheath entrance preventing portion may be a cut portion, formed by removing a portion of the light output surface.

Alternatively, the reflected light sheath entrance preventing portion may be a light transmittance preventing portion which is provided on a portion of the light output surface. Specific examples of such a light transmittance preventing portion may be selected from a group consisting of: a light absorbing film, a light reflecting film, and a light scattering surface.

Further, it is desirable for the OCT probe of the present invention to be equipped with: a lens having a reflecting surface for totally reflecting the light beam from the optical fiber to change the propagating direction thereof at substantially a right angle, and a convex spherical surface for focusing and outputting the light from the reflecting surface.

Still further, it is desirable for the OCT probe of the present invention to be of a configuration wherein:

the optical fiber is constituted by a first single mode optical fiber and a second optical fiber having a single refractive index structure, the first single mode optical fiber and the second optical fiber being connected at the ends thereof;

the end of the second optical fiber opposite the end which is connected to the first single mode optical fiber is fused to form a fused portion;

a lens is integrally formed at the fused portion or mounted onto the fused portion;

the refractive index of the second optical fiber is set to be equal to the refractive index of the core of the first single mode optical fiber;

the refractive index of the fused portion is set to be equal to the refractive index of the second optical fiber;

the refractive index of the lens is set to be equal to the refractive index of the second optical fiber;

the fused portion and the lens both are of shapes having a spherical portion at a part thereof;

the radius r2 of the spherical portion of the fused portion, the radius r1 of the spherical portion of the lens, the radius $\omega 0$ of the core of the first single mode optical fiber, the wavelength $\lambda$ of the light that propagates through the optical fibers in a vacuum, the refractive index n of the second optical fiber with respect to the wavelength $\lambda$, the length d0 that the light beam travels from the end of the second optical fiber to the light emitting edge of the lens, the outer diameter $\phi$ coreless of the second optical fiber, and the radius $\omega$ coreless of the light beam at the end of the second optical fiber toward the fused portion satisfy Formula 1 below:

$$\omega_{coreless} = \omega 0 \cdot \sqrt{1 + \left[\frac{\lambda\left\{d0 - 2r1 - r2 - \sqrt{r2^2 - \left(\frac{\phi_{coreless}}{2}\right)^2}\right\}}{\pi \cdot n \cdot \omega^2 0}\right]^2};$$

and the inequality r2>$\omega$ coreless; in the case that:

the reflecting surface is formed at a portion of the lens;

the reflected light sheath entrance preventing portion is formed at a portion of the lens separate from the reflecting surface; and the location at which the reflected light sheath entrance preventing portion is formed is a portion of the lens which is on the optical path of light which is reflected by the inner surface of the sheath.

Note that it is desirable for the outer diameters of the first single mode optical fiber and the second optical fiber to be substantially the same.

Alternatively, a configuration may be adopted in which the OCT probe of the present invention is equipped with:

a sleeve, which is inserted into the sheath after the optical fibers are inserted therethrough; wherein:

a light absorbing adhesive is used to adhesively attach the inner periphery of the sleeve and the outer peripheries of the optical fibers; and the light absorbing adhesive functions as the reflected light sheath entrance preventing portion.

It is desirable for an anti reflection coating to be formed on the light output surface of the optical system, the anti reflection coating being non reflective with respect to light that enters the light output surface.

Note that the preferred OCT probe of the present invention may be produced by the method described below. The method comprises the steps of:

connecting the first single mode optical fiber and the second optical fiber, of which the initial length L is set according to Formula 2 below:

$$L = \frac{\frac{4}{3}\pi(r1^3 + r2^3) + \pi \cdot \phi_{coreless}^2\left\{d0 - 2r1 - r2 - \sqrt{r2^2 - \left(\frac{\phi_{coreless}}{2}\right)^2}\right\}}{\pi \cdot \phi_{coreless}^2},$$

at the ends thereof;

fusing the end of the second optical fiber opposite the end which is connected to the first single mode optical fiber to form a spherical fused portion having the aforementioned radius r2;

integrally forming a lens at the fused portion by further fusing the fused portion, or mounting a separate lens onto the fused portion;

forming a planar reflecting surface at a portion of the lens, and cutting another portion of the lens different from the reflecting surface to form the reflected light sheath entrance preventing portion.

In this method, it is desirable for fusion of the end of the second optical fiber to be performed by electrical discharge, and for an electric discharge section to be moved toward the first single mode optical fiber, to form the fused portion.

According to the OCT probe of the present invention, the optical system is equipped with the light output surface that outputs light from the reflecting surface obliquely with respect to the inner surface of the sheath, and the reflected light sheath entrance preventing portion that prevents light which has been reflected by the inner surface of the sheath from reaching the reflecting surface through the light output surface. Therefore, multiple reflection of light which has been reflected by the inner surface of the sheath in the interior of the probe is prevented, and accordingly, the generation of ghost images due to multiple reflection can be positively prevented.

In the case that the OCT probe of the present invention is configured in the preferred mode described above, the light beam that propagates through the second optical fiber can be magnified to be greater than or equal to the outer diameter of the second optical fiber within fused portion, and further magnified by the lens. Therefore, a beam diameter $\omega d0$ at the light output surface of the lens can be magnified to a great degree. Thereby, the restriction of the relationship between the beam waist of the propagating light beam (which becomes the spot size of the light beam irradiated onto subjects) and the distance from the light output surface of the lens to the beam waist (the work distance) is resolved. Accordingly, realization of smaller spot sizes and longer work distances becomes possible.

Also, in the preferred mode of the OCT probe of the present invention, the refractive indices of the core of the first single mode optical fiber, the second optical fiber, the fused portion, and the lens are set to be equal. Therefore, multiple reflection at the interfaces among these optical elements can be prevented. This point also contributes to the prevention of the generation of ghost images due to multiple reflection.

Further, in the preferred mode of the OCT probe of the present invention, the outer diameter of the first single mode optical fiber and the outer diameter of the second optical fiber are matched. Therefore, adjustments of the optical axes of the optical fibers with respect to each other are facilitated.

In addition, a configuration is adopted such that the light beam that propagates through the second optical fiber is magnified within the fused portion to be greater or equal to the outer diameter of the second optical fiber. Therefore, the need to set the outer diameter of the second optical fiber to be large is obviated, and it becomes possible to miniaturize the portion of the OCT endoscopic probe that houses the optical fibers.

In the OCT probe of the present invention, the anti reflection coating, which is non reflective with respect to light that enters the light output surface, may be formed on the light output surface of the optical system. In this case, reflection of the propagating light at the light output surface is prevented, and accordingly multiple reflection is further suppressed, and the generation of ghost images can be positively prevented.

BEST MODE FOR CARRYING OUT THE INVENTION

Hereinafter, embodiments of the present invention will be described in detail, with reference to the attached drawings.

FIG. 1 through FIG. 5 illustrate an OCT probe according to a first embodiment of the present invention. First, as illustrated in FIG. 1A, a lensed optical fiber 1, which constitutes the OCT probe of the first embodiment, is constituted by: a first optical fiber 2, which is a single mode fiber; a second optical fiber 3, which is a non doped silica fiber; a fused portion 4; and a lens 5 constituted by non doped silica, for example. Note that FIG. 1B is a diagram that illustrates the specific dimensions of the structure of FIG. 1A, from which the reference numerals have been omitted from each of the elements.

The first optical fiber 2 is a single mode optical fiber equipped with a core 2a, for propagating light, and a cladding layer 2b which is formed around the periphery of the core 2a and which has a lower refractive index than the core 2a. On the other hand, the second optical fiber 3 is constituted by a non doped silica material with a coreless structure having a single refractive index. The refractive index of the second optical fiber 3 is set to be equal to the refractive index of the core 2a of the first optical fiber 2. The outer diameter φ coreless (refer to FIG. 1B) is set to be greater than or equal to the outer diameter of the first optical fiber 2. The first optical fiber 2 and the second optical fiber 3 are connected to each other at the ends thereof by fusion, for example. Note that as an example, the second optical fiber 3 is constituted by cylindrical silica glass having an outer diameter φ coreless within a range from 125 μm to 200 μm.

The fused portion 4 is formed by fusing the end of the second optical fiber 3 opposite the end which is connected to the first optical fiber 2. The shape of the fused portion 4 is such that a spherical portion having a radius r2 is included at a portion thereof. The radius r2 is set to a value greater than a beam radius ω coreless, which is the beam radius at the end of the second optical fiber at the end thereof toward the fused portion 4. The refractive index of the fused portion 4 is equal to the refractive index of the second optical fiber 3.

The lens 5, having a radius r1 which is greater than the radius of the second optical fiber 3 (φ coreless/2), is formed on the fused portion 4 at the side thereof opposite the second optical fiber 3. As will be described later, the lens 5 is either formed integrally with the fused portion 4, or formed as a separate component then coupled to the fused portion 4. The refractive index of the lens 5 is set to be equal to the refractive index of the second optical fiber 3. That is, the refractive indices of the core 2a of the first optical fiber 2, the second optical fiber 3, and the lens 5 are equal.

The shape of the lens 5 is initially a spherical lens, of which the radius r1 is 500 μm. However, a planar reflecting surface 5a is formed at a portion thereof by optical polishing, for example, such that the planar reflecting surface 5a passes through the center of the sphere. Further, another planar surface 5b is formed separately from the reflecting surface 5a, also by optical polishing, for example. Accordingly, the final shape of the lens 5 is that which includes a spherical portion having the radius of r1.

A reflective film (not shown) is formed on the reflecting surface 5a, or a mirror polishing process is administered thereon. In the case that mirror polishing is performed, a portion of the lens 5 is cut to form a planar surface, then the cut surfaced is mechanically polished to obtain a mirror finish. On the other hand, in the case that a reflective film is formed, metal films that exhibit high reflectance, such as aluminum, nickel, gold, and silver, or dielectric multilayer films are formed onto the cut surface. The film may be formed by vapor deposition, sputtering, CVD, plating, coating, or the like. Further, an AR (Anti Reflection) coating is provided on a light input/output surface 5c (the output surface for propagating light) of the lens 5.

Figure 2:
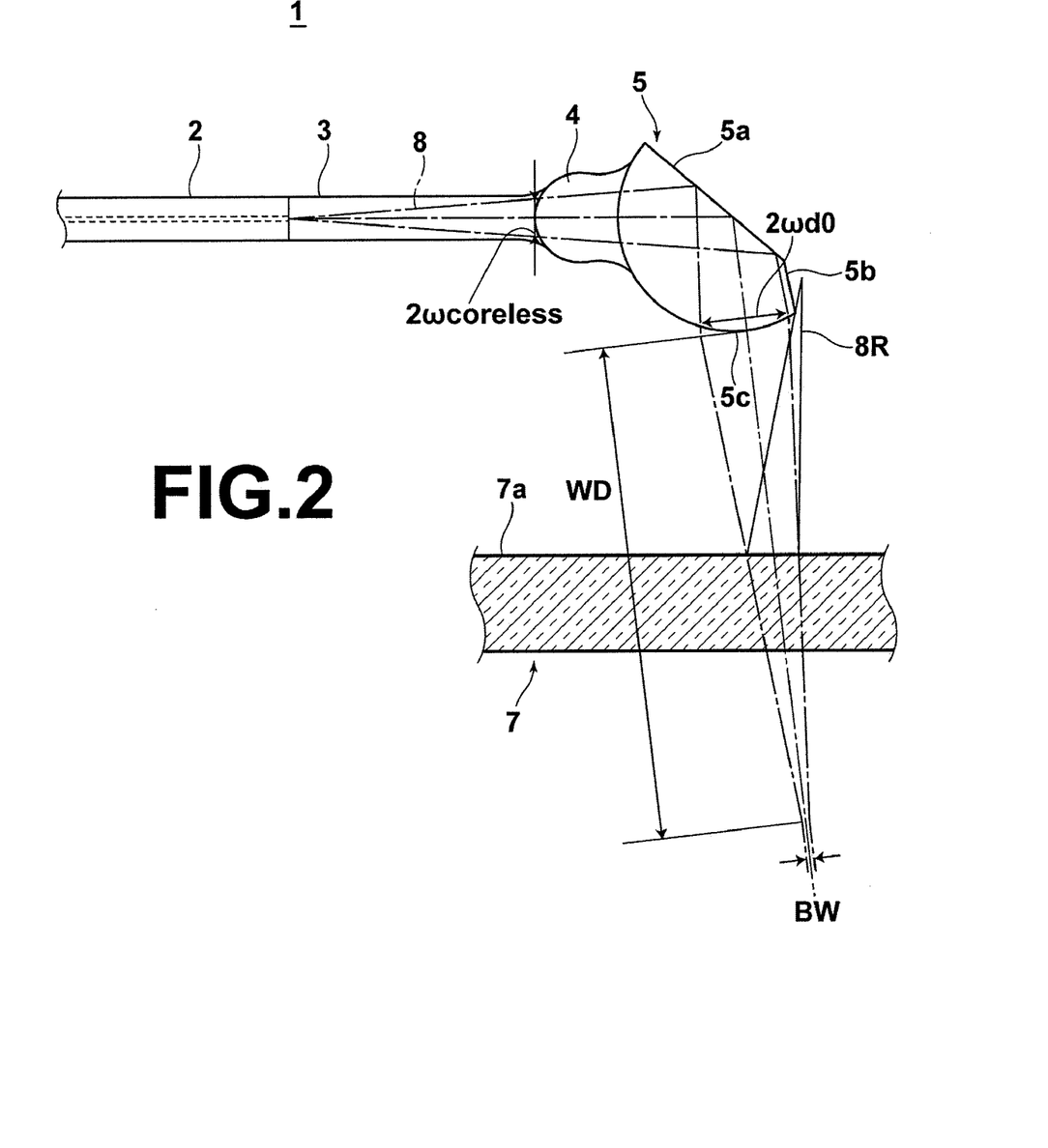
FIG. 2 is a schematic view that illustrates the propagation state of light within the lensed optical fiber of FIG. 1 and the propagation state of light reflected by a sheath.

The lensed optical fiber 1 is combined with other components to constitute the OCT endoscopic probe. FIG. 2 illustrates a sheath 7, which is one of the other components that constitute the OCT endoscopic probe, and the lensed optical fiber 1. The sheath 7 is a light transmissive cylindrical member having a closed distal end. The lensed optical fiber 1 is housed within the interior of the sheath 7. Note that the peripheral wall of the sheath 7 is illustrated in FIG. 2. In addition, propagating light is illustrated by broken lines in FIG. 2.

Hereinafter, the operation of the OCT endoscopic probe will be described with reference to FIG. 2. A light beam 8 is emitted from a light source (not shown), and propagates through the first optical fiber 2. The light beam 8 which is output from the first optical fiber 2 enters the interior of the second optical fiber 3 and continues to propagate while spreading, and enters the fused portion 4. The light beam 8 that enters the fused portion 4 is magnified further within the fused portion 4 due to the aforementioned relationship r2>ω coreless, and is magnified to be greater than or equal to the outer diameter φ coreless of the second optical fiber 3.

The light beam 8 then enters the lens 5, and the optical path thereof is changed by being reflected at the reflecting surface 5a. The reflected light beam 8 is focused at the light input/output surface (an output surface with respect to the light beam 8), and is output from the light input/output surface 5c as a converged light beam. The output converged light beam 8 is output through the sheath 7, which constitutes the tip of the OCT endoscopic probe, and is irradiated onto living tissue, which is a subject. At this time, a drive apparatus (not shown) rotates the lensed optical fiber 1 about the axis of the fiber, to scan the living tissue in a cylindrical direction with the light beam 8 output from the sheath 7.

A portion of the light which has been reflected or scattered by the surface or the interior of the living tissue travels along the optical path in the opposite direction, enters the lens 5, and returns to the side of the first optical fiber 2. The light which propagates back through the first optical fiber 2 is received by photodetectors such as photodiodes. Predetermined processes are administered to the photodetection signals, to obtain image signals that represent a tomographic image of the living tissue.

Figure 5:
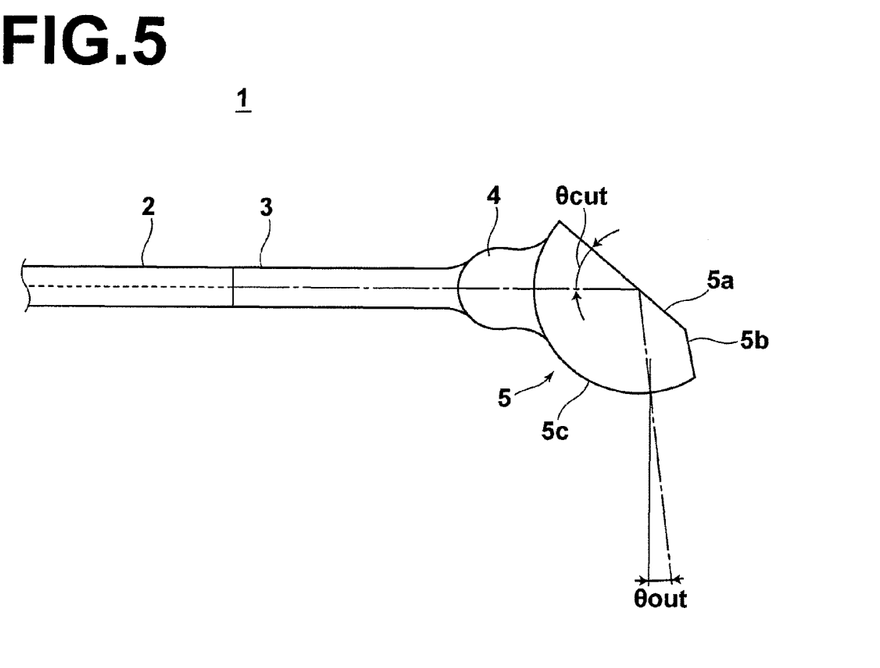
FIG. 5 is a schematic view that illustrates the light output state of the lensed optical fiber of FIG. 1.

Next, the shape of the lens 5 will be described in more detail, with combined reference to FIG. 5. When the angle θ out, at which the light is output from the light input/output surface 5c of the lens 5 is expressed as an angle with respect to a plane perpendicular to the longitudinal axis of the second optical fiber 3, the light output angle θ out is defined by Formula 3 as follows:

$$\theta out = 90° - 2\theta cut$$

In the above formula, θ cut is the angle at which the reflecting surface 5a is formed with respect to the longitudinal axis of the second optical fiber 3. The light output angle θ out is determined by the reflecting surface forming angle θ cut, based on the above formula. Note that in the first embodiment, the light output angle θ out is set to approximately 7 degrees, for example.

In addition, the beam radius ωdo (refer to FIG. 2) of the light beam at the light input/output surface 5c of the lens 5 can be derived by the Formula 4 below:

$$\omega d0 = \omega 0 \cdot \sqrt{1 + \left(\frac{\lambda \cdot d0}{\pi \cdot n \cdot \omega^2 0}\right)^2}$$

wherein: ω0 is the core radius of the first optical fiber 2; λ is the wavelength of the light beam; n is the refractive index of the second optical fiber 3 with respect to the wavelength λ; and d0 is the distance that the light beam propagates from the end of the second optical fiber 3 to the lens 5.

Accordingly, the location at which the planar surface 5b is formed on the lens 5 is most preferably a location outside of the beam radius ωdo of the light beam at the light input/output surface 5c. However, the location at which the planar surface 5b is formed is not limited to the most preferred mode. Slight vignetting of the light beam which is output from the light input/output surface 5c by the planar surface 5b being formed is acceptable.

Figure 1A:
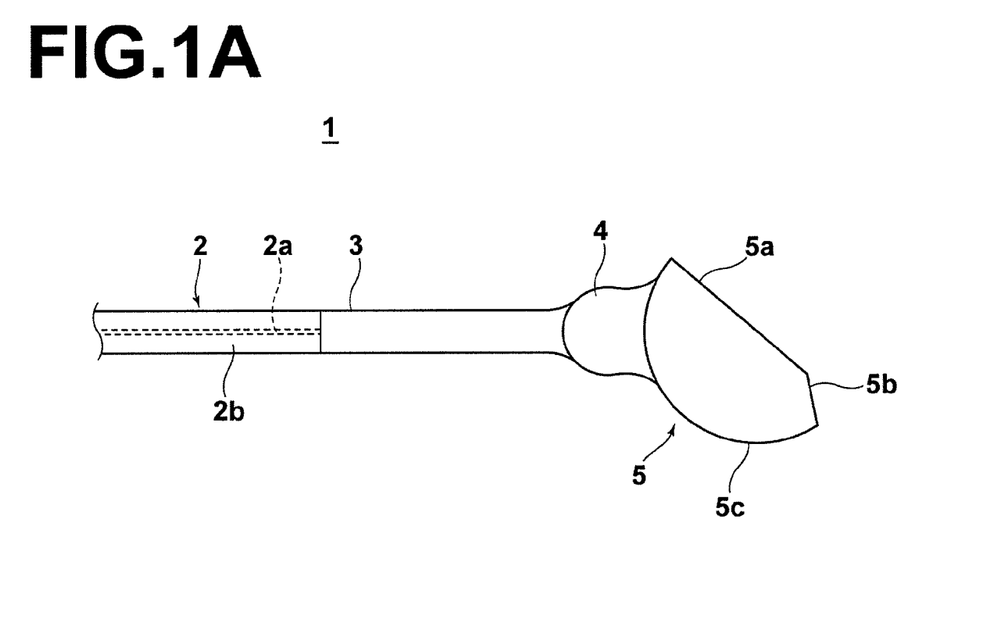
FIG. 1A and FIG. 1B are side views that illustrate a lensed optical fiber that constitutes an OCT probe according to a first embodiment of the present invention.
Figure 1B:
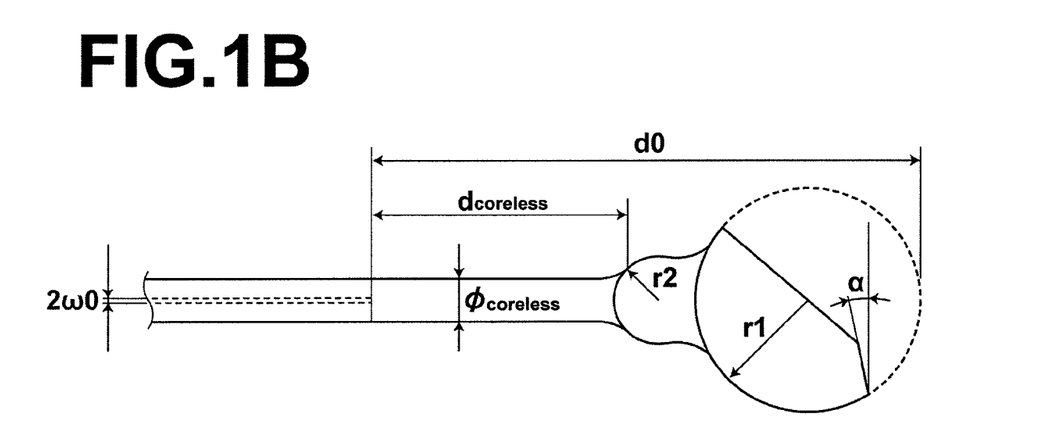

Further, the length d coreless (refer to FIG. 1B) of the second optical fiber 3 is derived by the Formula 5 below:

$$d_{coreless} = d0 - 2r1 - r2 - \sqrt{r2^2 - \left(\frac{\phi_{coreless}}{2}\right)^2}$$

wherein: r1 is the radius of the lens 5; and φ coreless is the outer diameter of the second optical fiber 3.

From Formula 1 and Formula 2 above, it is necessary to set the radius r2 of the fused portion to be greater than the value of ω coreless, which is defined by Formula 6 below:

$$\omega_{coreless} = \omega 0 \cdot \sqrt{1 + \left[\frac{\lambda \left\{d0 - 2r1 - r2 - \sqrt{r2^2 - \left(\frac{\phi_{coreless}}{2}\right)^2}\right\}}{\pi \cdot n \cdot \omega^2 0}\right]^2}$$

Here, a portion of the light which is output from the light input/output surface 5c of the lens 5 is reflected by the inner surface of the sheath 7, as illustrated in FIG. 2. The reflected light 8R is illustrated by solid lines in FIG. 2. The reflected light 8R travels toward the lens 5, but a portion of the lens 5 along the optical path of the reflected light 8R is cut, to form the planar surface 5b (more specifically, a portion of the lens 5 is cut so as to remove a portion of the light input/output surface 5c). By cutting the lens 5 in this manner, a reflected light sheath entrance preventing portion that prevents the reflected light 8R from entering the lensed optical fiber 1 is formed. Therefore, multiple reflection of propagating light beams within the OCT endoscopic probe is prevented, and accordingly, the generation of the aforementioned ghost images is prevented. Generally, multiple reflection can be effectively suppressed by setting the forming angle α of the planar surface 5b (refer to FIG. 1B) to 10 degrees.

Further, in the OCT probe according to the first embodiment, the refractive indices of the core 2a of the first optical fiber 2, the second optical fiber 3, the fused portion 4, and the lens 5 are set to be equal. Therefore, reflection of the propagating light is limited to that at the reflecting surface 5a, and multiple reflection at the interfaces among these optical elements can be prevented. This point also contributes to the prevention of the generation of ghost images due to multiple reflection.

Still further, in the OCT probe according to the first embodiment, the anti reflection coating is formed on the light input/output surface 5c of the lens 5. Thereby, reflection of the propagating light at the light input/output surface 5c is prevented, and accordingly multiple reflection is further suppressed.

In addition, in the OCT probe according to the first embodiment, the fused portion 4 is formed on the second optical fiber 3, which is a light introducing portion. The propagating light beam is magnified within the fused portion 4 to be greater than or equal to outer diameter φ coreless of the second optical fiber 3, and further magnified by the lens 5. Therefore, the beam diameter ωd0 at the light input/output surface 5c of the lens 5 can be magnified to a great degree. Thereby, the restriction of the relationship between the beam waist BW of the propagating light beam 8 illustrated in FIG. 2 and the distance from the light output surface of the lens 5 to the beam waist (the work distance WD) is resolved. Accordingly, realization of smaller beam waists BW and longer work distances WD becomes possible.

As described previously, the radius r2 of the fused portion 4 needs only to be greater than the beam radius ω coreless of the light beam at the end of the second optical fiber 3 toward the fused portion 4. Therefore, adjustments to the aforementioned propagation length d0 (refer to FIG. 1B) can be easily performed, by the forming conditions of the fused portion 4 (heating and fusion of the end of the second optical fiber 3) and adjustments to the radius r2 thereof. Further, control of the radius r1 of the lens 5 and the propagation length d0 is also facilitated.

Because no optical components other than the lensed optical fiber 1 are necessary to magnify the propagating light beam 8, production cost can be reduced and yield can be improved, due to the reduction in the number of parts.

Further, in the OCT probe according to the first embodiment of the present invention, the outer diameter of the first optical fiber 2 and the outer diameter ω coreless of the second optical fiber 3 are matched. Therefore, an advantageous effect, that adjustments of the optical axes of the optical fibers with respect to each other are facilitated, is obtained. In addition, a configuration is adopted such that the propagating light beam is magnified within the fused portion 4 to be greater or equal to the outer diameter φ coreless of the second optical fiber 3. Therefore, the need to set the outer diameter φ coreless of the second optical fiber 3 to be large is obviated, and it becomes possible to employ a smaller diameter lensed optical fiber 1 and to miniaturize the portion of the OCT endoscopic probe that houses the lensed optical fiber 1.

Figure 3A:
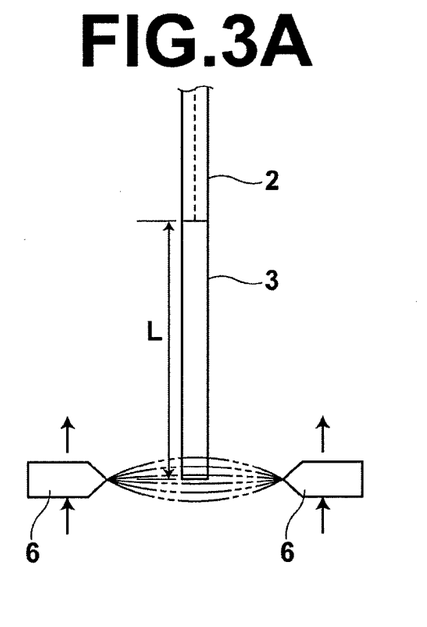
FIG. 3A, FIG. 3B, FIG. 3C, and FIG. 3D are diagrams that schematically illustrate a portion of the steps for producing the lensed optical fiber of FIG. 1.

Next, a method for producing the lensed optical fiber 1 having the configuration described above will be described with reference to FIG. 3 and FIG. 4. First, the first optical fiber 2 and the second optical fiber 3 are connected by fusing. Thereafter, the end of the second optical fiber 3 opposite the first optical fiber 2 is inserted into a discharge field of an arc discharge section 6, as illustrated in FIG. 3A. The discharge fuses the end of the second optical fiber 3, and the fused portion 4 is formed automatically. The initial length L of the second optical fiber 3 prior to this fusion is set according to Formula 2 below:

$$L = \frac{\frac{4}{3}\pi(r1^3 + r2^3) + \pi \cdot \phi_{coreless}^2 \left\{ d0 - 2r1 - r2 - \sqrt{r2^2 - \left(\frac{\phi_{coreless}}{2}\right)^2} \right\}}{\pi \cdot \phi_{coreless}^2}.$$

The spherical fused portion 4 is formed by moving the discharge section 6 toward the side of the first optical fiber 2 such that the fused portion 4 is of the predetermined radius r2 during the arc discharge. By moving the discharge section 6 while keeping the second optical fiber 3 immobilized, control of the radius r2 of the fused portion 4 to predetermined dimensions is facilitated. As described previously, the radius r2 of the fused portion 4 is set to be greater than the beam radius ω coreless in the second optical fiber 3 at the end toward the fused portion 4. Note that here, arc discharge was described as an example of the heating method of the second optical fiber 3. Alternatively, other heating/fusion methods such as image heating and resistance heating may be employed.

Figure 3B:
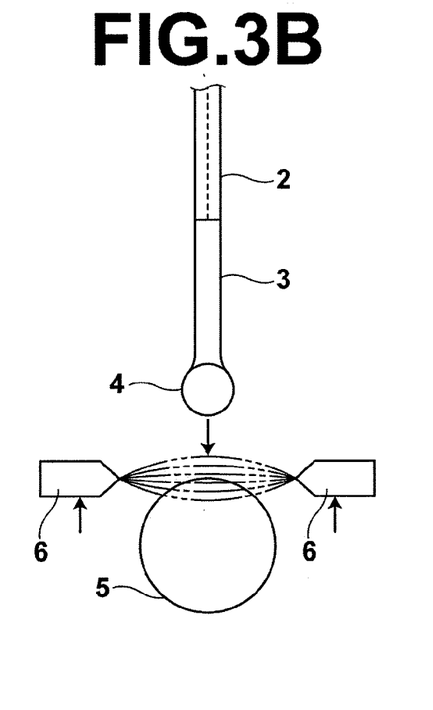

FIG. 3B is a conceptual view that illustrates a state in which the spherical fused portion 4 is formed at the end of the second optical fiber 3. By adjusting the initial length L of the second optical fiber 3 according to the propagation optical path of the lensed optical fiber 1, the radius r2 of the fused portion can be set to a desired value regardless of the diameter φ coreless of the second optical fiber 3.

Figure 3C:
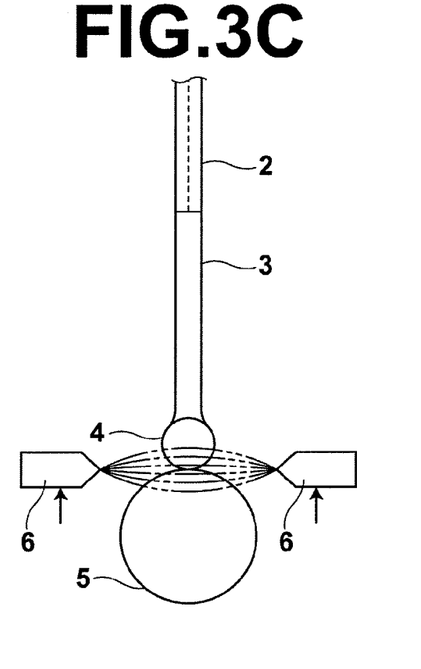
Figure 3D:
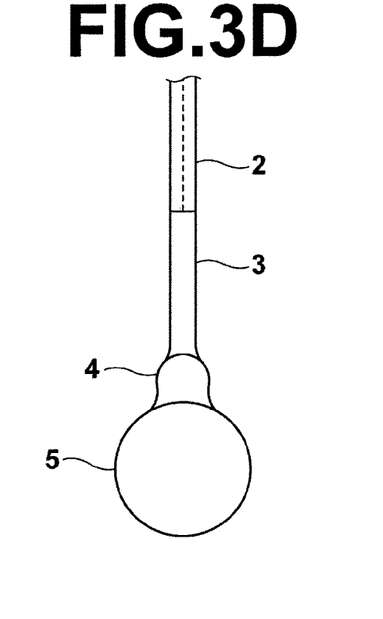

Next, the peak of the spherical lens 5 is heated by being inserted into the arc discharge field as illustrated in FIG. 3B. Then, the peak of the fused portion 4 is heated by being inserted into the arc discharge field as illustrated in FIG. 3C. The heated peaks of the spherical lens 5 and the fused portion 4 are placed into point contact as illustrated in FIG. 3C, to couple the spherical lens 5 and the fused portion 4 at the point at the peaks thereof, as illustrated in FIG. 3D. At this time, the radius r1 of the spherical lens 5 does not change, and only the fused portion 4 is fused to be coupled with the spherical lens 5, because the volume of the fused portion 4 is smaller than that of the spherical lens 5.

Note that the method of production is not limited to that described above. Alternatively, the spherical lens 5 may be formed by further fusing the fused portion 4 after producing the spherical fused portion 4.

Figure 4A:
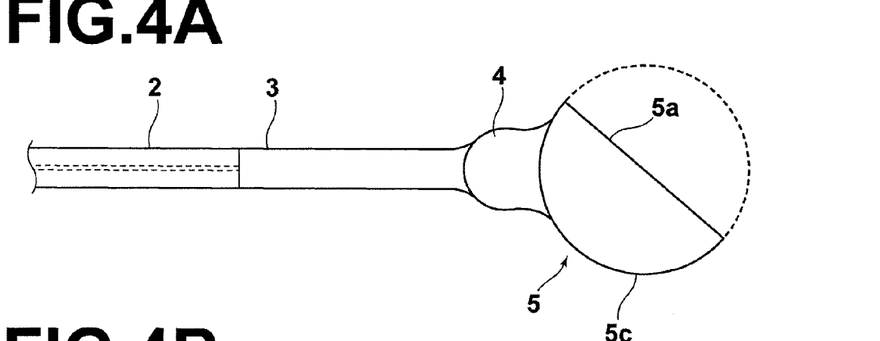
FIG. 4A and FIG. 4B are diagrams that schematically illustrate a different portion of the steps for producing the lensed optical fiber of FIG. 1.
Figure 4B:
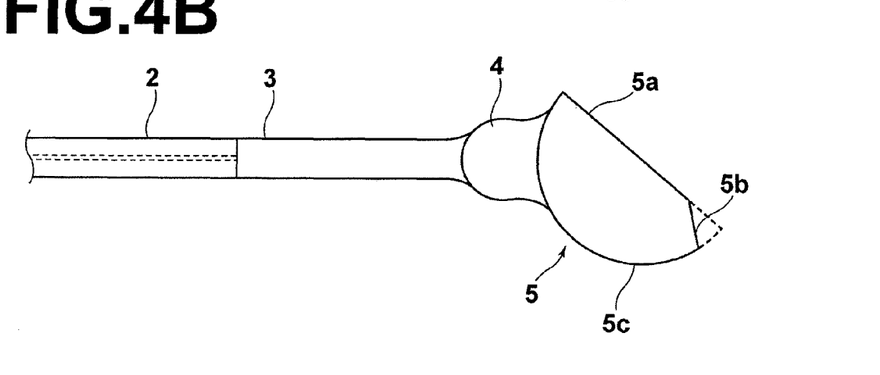

Next, the planar reflecting surface 5a is formed at a portion of the spherical lens 5, as illustrated in FIG. 4A. Further, the planar surface 5b is formed at a portion of the spherical lens 5 separate from the reflecting surface 5a, as illustrated in FIG. 4B. Still further, the anti reflection coating is formed on the light input/output surface 5c.

In the method described above, the lens 5 is integrated with the second optical fiber 3 via the fused portion 4. Therefore, even if the radius r1 of the lens 5 is great, the coupling area with the fused portion 4 relative to the surface area of the lens 5 is great. Accordingly, sufficient coupling strength can be obtained between the second optical fiber 3 and the lens 5, and larger diameter lenses 5 can be utilized. Further, control of the inclination of the optical axis of the lens 5 with respect to central axis of the core of the first optical fiber 2 is also facilitated.

In this method, no special steps other than production of the lensed optical fiber 1 are necessary to form a structure for magnifying the propagating light beam. Therefore, cost reductions can be realized due to the reduced number of production steps and time required for production. In addition, it is possible to produce the lensed optical fiber 1 using a common fusing device. Therefore, it is not necessary to utilize fusing devices having different sizes, and installation costs can also be suppressed.

Note that the method for producing the OCT probe of the present invention is not limited to that described above, and various changes and modifications are possible. For example, the fused portion 4 may be produced by a molding process, then the fused portion 4 and the lens 5 may be coupled by an optical adhesive. In this case, an optical adhesive having a refractive index substantially equal to the refractive index of the second optical fiber 3 is employed. However, as described in the first embodiment, direct integration of the second optical fiber 3 and the lens 5, which have the same refractive index, via the fused portion 4 is superior from the viewpoints of reliability, durability, and loss properties of propagating light.

Further, the OCT probe of the present invention is not limited to a configuration which is equipped with the spherical lens 5 illustrated in FIG. 1. Alternatively, the OCT probe of the present invention may be configured to have the basic configuration of the conventional OCT probe illustrated in FIG. 7, for example. That is, in this case, a cut portion is formed at a portion of a prism 26, to provide the reflected light sheath entrance preventing portion. As a further alternative, a light transmittance preventing portion may be formed by a light absorbing film, a light reflecting film, or a light scattering surface, and be employed as the reflected light sheath entrance preventing portion. Note that forming the light transmittance preventing portion and employing it as the reflected light sheath entrance preventing portion is also applicable to the spherical lens 5 illustrated in FIG. 1 as well.

Figure 8:
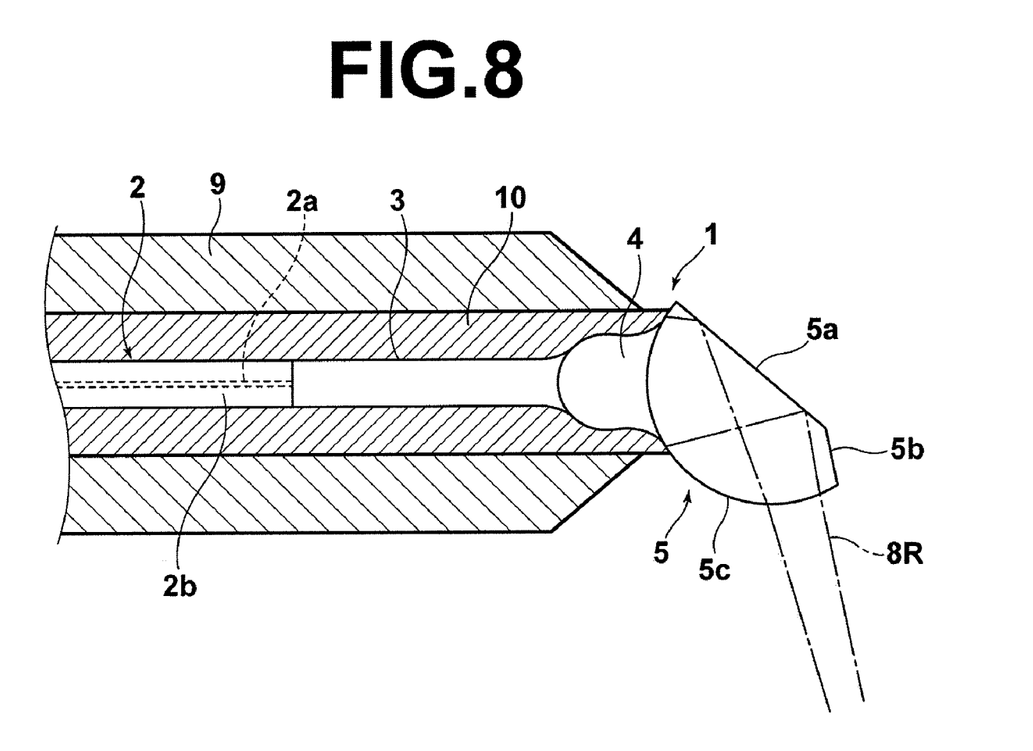
FIG. 8 is a side view that illustrates a lensed optical fiber that constitutes an OCT probe according to a second embodiment of the present invention.

Next, a second embodiment of the present invention will be described with reference to FIG. 8. Note that in FIG. 8, elements which are the same as those illustrated in FIG. 1 are denoted with the same reference numerals, and detailed descriptions thereof will be omitted. The lensed optical fiber 1 that constitutes the OCT probe according to the second embodiment is basically the same as that illustrated in FIG. 1. However, the first optical fiber 2, the second optical fiber 3, and the fused portion 4 are inserted within a cylindrical sleeve 9. The outer peripheral portions of the first optical fiber 2, the second optical fiber 3, and the fused portion 4 are fixed to the inner peripheral portion of the sleeve 9 by an adhesive 10. Note that the sleeve 9, which holds the lensed optical fiber 1 therein, is inserted within the sheath 7 illustrated in FIG. 2.

Here, a light absorbing adhesive is employed as the adhesive 10. In the second embodiment, the adhesive 10 is employed as the reflected light sheath entrance preventing portion. Carbon black may be added to impart light absorbing properties to the adhesive 10. Because the outer periphery of the lensed optical fiber 1 is covered by the adhesive 10, even if the reflected light 8R, which is reflected at the inner surface 7a of the sheath 7 (refer to FIG. 7) enters the lensed optical fiber 1, the reflected light 8R is absorbed by the interface between the lensed optical fiber 1 and the adhesive 10. Accordingly, generation of ghost images is prevented.

What is claimed is:

1. An OCT probe, comprising:
   a sheath to be inserted into a subject;
   an optical system provided within the sheath, for changing the direction of a light beam which has propagated from a light source through an optical fiber with a reflecting surface to irradiate the light beam onto the subject through a transparent portion of the sheath, and for reflecting the light beam, which has been reflected by the subject, at the reflecting surface to guide the light beam into the optical fiber;
   a light output surface, which is a part of the optical system, for causing the light beam to be output from the reflecting surface in a direction obliquely inclined with respect to the inner surface of the sheath; and
   a reflected light sheath entrance preventing portion, which is a part of the optical system, for preventing light reflected by the inner surface of the sheath from entering the optical fiber.

2. An OCT probe as defined in claim 1, wherein:
   the reflected light sheath entrance preventing portion is a cut portion, formed by removing a portion of the light output surface.

3. An OCT probe as defined in claim 1, wherein:
   the reflected light sheath entrance preventing portion is a light transmittance preventing portion which is provided on a portion of the light output surface.

4. An OCT probe as defined in claim 3, wherein:
   the light transmittance preventing portion is an element selected from among a group consisting of: a light absorbing film, a light reflecting film, and a light scattering surface.

5. An OCT probe as defined in claim 1, wherein the optical system comprises:
   a lens having a reflecting surface for totally reflecting the light beam from the optical fiber to change the propagating direction thereof at substantially a right angle, and a convex spherical surface for focusing and outputting the light from the reflecting surface.

6. An OCT probe as defined in claim 2, wherein the optical system comprises:
   a lens having a reflecting surface for totally reflecting the light beam from the optical fiber to change the propagating direction thereof at substantially a right angle, and a convex spherical surface for focusing and outputting the light from the reflecting surface.

7. An OCT probe as defined in claim 3, wherein the optical system comprises:
   a lens having a reflecting surface for totally reflecting the light beam from the optical fiber to change the propagating direction thereof at substantially a right angle, and a convex spherical surface for focusing and outputting the light from the reflecting surface.

8. An OCT probe as defined in claim 4, wherein the optical system comprises:
   a lens having a reflecting surface for totally reflecting the light beam from the optical fiber to change the propagating direction thereof at substantially a right angle, and a convex spherical surface for focusing and outputting the light from the reflecting surface.

9. An OCT probe as defined in claim 1, wherein:
   the optical fiber is constituted by a first single mode optical fiber and a second optical fiber having a single refractive index structure, the first single mode optical fiber and the second optical fiber being connected at the ends thereof;
   the end of the second optical fiber opposite the end which is connected to the first single mode optical fiber is fused to form a fused portion;
   a lens is integrally formed at the fused portion or mounted onto the fused portion;
   the refractive index of the second optical fiber is set to be equal to the refractive index of the core of the first single mode optical fiber;
   the refractive index of the fused portion is set to be equal to the refractive index of the second optical fiber;
   the refractive index of the lens is set to be equal to the refractive index of the second optical fiber;
   the fused portion and the lens both are of shapes having a spherical portion at a part thereof;
   the reflecting surface is formed at a portion of the lens;
   the reflected light sheath entrance preventing portion is formed at a portion of the lens separate from the reflecting surface;
   the location at which the reflected light sheath entrance preventing portion is formed is a portion of the lens which is on the optical path of light which is reflected by the inner surface of the sheath;
   the radius $r_2$ of the spherical portion of the fused portion, the radius $r_1$ of the spherical portion of the lens, the radius $\omega_0$ of the core of the first single mode optical fiber, the wavelength $\lambda$ of the light that propagates through the optical fibers in a vacuum, the refractive index n of the second optical fiber with respect to the wavelength $\lambda$, the length $d_0$ that the light beam travels from the end of the second optical fiber to the light emitting edge of the lens, the outer diameter $\phi$ coreless of the second optical fiber, and the radius $\omega$ coreless of the light beam at the end of the second optical fiber toward the fused portion satisfy the equation:

$$\omega_{coreless} = \omega 0 \cdot \sqrt{1 + \left[\frac{\lambda \left\{d0 - 2r1 - r2 - \sqrt{r2^2 - \left(\frac{\phi_{coreless}}{2}\right)^2}\right\}}{\pi \cdot n \cdot \omega^2 0}\right]^2} \ ;$$

and the inequality r2>ω coreless.

10. An OCT probe as defined in claim 2, wherein:
the optical fiber is constituted by a first single mode optical fiber and a second optical fiber having a single refractive index structure, the first single mode optical fiber and the second optical fiber being connected at the ends thereof;
the end of the second optical fiber opposite the end which is connected to the first single mode optical fiber is fused to form a fused portion;
a lens is integrally formed at the fused portion or mounted onto the fused portion;
the refractive index of the second optical fiber is set to be equal to the refractive index of the core of the first single mode optical fiber;
the refractive index of the fused portion is set to be equal to the refractive index of the second optical fiber;
the refractive index of the lens is set to be equal to the refractive index of the second optical fiber;
the fused portion and the lens both are of shapes having a spherical portion at a part thereof;
the reflecting surface is formed at a portion of the lens;
the reflected light sheath entrance preventing portion is formed at a portion of the lens separate from the reflecting surface;
the location at which the reflected light sheath entrance preventing portion is formed is a portion of the lens which is on the optical path of light which is reflected by the inner surface of the sheath;
the radius r2 of the spherical portion of the fused portion, the radius r1 of the spherical portion of the lens, the radius ω0 of the core of the first single mode optical fiber, the wavelength λ of the light that propagates through the optical fibers in a vacuum, the refractive index n of the second optical fiber with respect to the wavelength λ, the length d0 that the light beam travels from the end of the second optical fiber to the light emitting edge of the lens, the outer diameter φ coreless of the second optical fiber, and the radius ω coreless of the light beam at the end of the second optical fiber toward the fused portion satisfy the equation:

$$\omega_{coreless} = \omega 0 \cdot \sqrt{1 + \left[\frac{\lambda \left\{d0 - 2r1 - r2 - \sqrt{r2^2 - \left(\frac{\phi_{coreless}}{2}\right)^2}\right\}}{\pi \cdot n \cdot \omega^2 0}\right]^2} \ ;$$

and the inequality r2>ω coreless.

11. An OCT probe as defined in claim 3, wherein:
the optical fiber is constituted by a first single mode optical fiber and a second optical fiber having a single refractive index structure, the first single mode optical fiber and the second optical fiber being connected at the ends thereof;
the end of the second optical fiber opposite the end which is connected to the first single mode optical fiber is fused to form a fused portion;
a lens is integrally formed at the fused portion or mounted onto the fused portion;
the refractive index of the second optical fiber is set to be equal to the refractive index of the core of the first single mode optical fiber;
the refractive index of the fused portion is set to be equal to the refractive index of the second optical fiber;
the refractive index of the lens is set to be equal to the refractive index of the second optical fiber;
the fused portion and the lens both are of shapes having a spherical portion at a part thereof;
the reflecting surface is formed at a portion of the lens;
the reflected light sheath entrance preventing portion is formed at a portion of the lens separate from the reflecting surface;
the location at which the reflected light sheath entrance preventing portion is formed is a portion of the lens which is on the optical path of light which is reflected by the inner surface of the sheath;
the radius r2 of the spherical portion of the fused portion, the radius r1 of the spherical portion of the lens, the radius ω0 of the core of the first single mode optical fiber, the wavelength λ of the light that propagates through the optical fibers in a vacuum, the refractive index n of the second optical fiber with respect to the wavelength λ, the length d0 that the light beam travels from the end of the second optical fiber to the light emitting edge of the lens, the outer diameter φ coreless of the second optical fiber, and the radius ω coreless of the light beam at the end of the second optical fiber toward the fused portion satisfy the equation:

$$\omega_{coreless} = \omega 0 \cdot \sqrt{1 + \left[\frac{\lambda \left\{d0 - 2r1 - r2 - \sqrt{r2^2 - \left(\frac{\phi_{coreless}}{2}\right)^2}\right\}}{\pi \cdot n \cdot \omega^2 0}\right]^2} \ ;$$

and the inequality r2>ω coreless.

12. An OCT probe as defined in claim 9, wherein:
the outer diameters of the first single mode optical fiber and the second optical fiber are substantially the same.

13. An OCT probe as defined in claim 10, wherein:
the outer diameters of the first single mode optical fiber and the second optical fiber are substantially the same.

14. An OCT probe as defined in claim 11, wherein:
the outer diameters of the first single mode optical fiber and the second optical fiber are substantially the same.

15. An OCT probe as defined in claim 1, wherein:
a sleeve is provided, which is inserted into the sheath after the optical fibers are inserted therethrough;
a light absorbing adhesive is used to adhesively attach the inner periphery of the sleeve and the outer peripheries of the optical fibers; and
the light absorbing adhesive functions as the reflected light sheath entrance preventing portion.

16. An OCT probe as defined in claim 2, wherein:
a sleeve is provided, which is inserted into the sheath after the optical fibers are inserted therethrough;
a light absorbing adhesive is used to adhesively attach the inner periphery of the sleeve and the outer peripheries of the optical fibers; and
the light absorbing adhesive functions as the reflected light sheath entrance preventing portion.

17. An OCT probe as defined in claim 3, wherein:
a sleeve is provided, which is inserted into the sheath after the optical fibers are inserted therethrough;

a light absorbing adhesive is used to adhesively attach the inner periphery of the sleeve and the outer peripheries of the optical fibers; and the light absorbing adhesive functions as the reflected light sheath entrance preventing portion.

18. An OCT probe as defined in claim 1, wherein:

an anti reflection coating is formed on the light output surface of the optical system.

19. An OCT probe as defined in claim 2, wherein:

an anti reflection coating is formed on the light output surface of the optical system.

20. An OCT probe as defined in claim 3, wherein:

an anti reflection coating is formed on the light output surface of the optical system.

* * * * *